United States Patent
Popescu

(10) Patent No.: US 11,815,575 B2
(45) Date of Patent: Nov. 14, 2023

(54) MAGNETIC RESONANCE IMAGING DEVICE, COMPUTER-IMPLEMENTED METHOD FOR OPERATING A MAGNETIC RESONANCE IMAGING DEVICE, COMPUTER PROGRAM AND ELECTRONICALLY READABLE STORAGE MEDIUM

(71) Applicant: Siemens Healthcare GmbH, Erlangen (DE)

(72) Inventor: Stefan Popescu, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 17/665,854

(22) Filed: Feb. 7, 2022

(65) Prior Publication Data

US 2022/0252685 A1    Aug. 11, 2022

(30) Foreign Application Priority Data

Feb. 8, 2021   (EP) .................................... 21155850

(51) Int. Cl.
   *G01R 33/385*    (2006.01)
   *A61B 5/055*    (2006.01)
   (Continued)

(52) U.S. Cl.
   CPC ............ *G01R 33/385* (2013.01); *A61B 5/055* (2013.01); *G01R 33/24* (2013.01); *G01R 33/58* (2013.01)

(58) Field of Classification Search
   CPC ...... G01R 33/385; G01R 33/24; G01R 33/58; A61B 5/055
   See application file for complete search history.

(56) References Cited

U.S. PATENT DOCUMENTS

| 5,055,791 A | 10/1991 | LeRoux et al. |
| 5,558,091 A * | 9/1996 | Acker ................. A61B 5/103 324/207.13 |

(Continued)

FOREIGN PATENT DOCUMENTS

| DE | 102018203845 A1 | 9/2019 |
| DE | 102020208180 A1 | 12/2021 |

(Continued)

OTHER PUBLICATIONS

M. A. Blanco et al., "Evaluation of rotation matrices in the basis of real spherical harmonics", Journal of Molecular Structure (Theochem) 419, pp. 19-27, (1997).

(Continued)

*Primary Examiner* — Dixomara Vargas
(74) *Attorney, Agent, or Firm* — Banner & Witcoff Ltd.

(57) ABSTRACT

A MRI device including a main field unit for establishing a main magnetic field (MF) in an imaging region, a gradient coil assembly for generating a gradient field in the imaging region, a RF arrangement for sending excitation signals to and receiving MR signals from the imaging region, a field camera for determining MF information in the imaging region, the field camera comprising multiple MF sensors arranged at measurement positions enclosing the imaging region, and a controller. The controller is configured to receive sensor data for each measurement positions, from the sensor data, calculate the MF information for the imaging region, and implement a calibration and/or correction measure depending on the MF information. The field camera may be a vector-field camera acquiring vector-valued sensor data describing the MF at each measurement positions three-dimensionally. The controller may determine the MF information to three dimensionally describe the MF in the imaging region.

15 Claims, 3 Drawing Sheets

Figure 1:
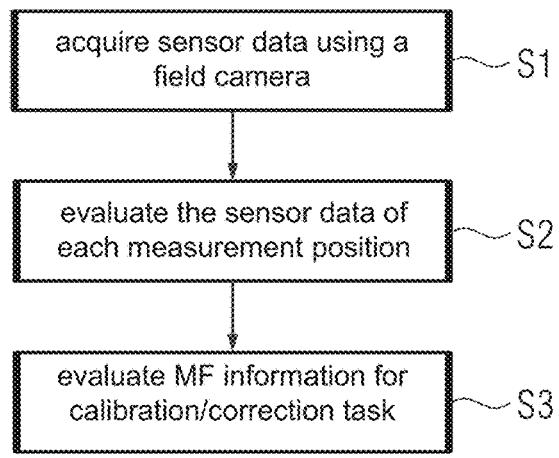

(51) Int. Cl.
*G01R 33/24* (2006.01)
*G01R 33/58* (2006.01)

(56) References Cited

U.S. PATENT DOCUMENTS

| 5,731,704 | A * | 3/1998 | Schnur ................. G01R 33/389 |
| | | | 324/319 |
| 6,800,913 | B2 | 10/2004 | Johnson et al. |
| 9,791,526 | B2 | 10/2017 | Barmet et al. |
| 10,018,690 | B2 | 7/2018 | Overweg et al. |
| 2005/0218892 | A1 | 10/2005 | Pruessmann et al. |
| 2007/0279060 | A1* | 12/2007 | Dannels ........... G01R 33/56563 |
| | | | 324/320 |
| 2009/0123048 | A1* | 5/2009 | Leroux ................. G06T 11/006 |
| | | | 250/363.04 |
| 2011/0156706 | A1* | 6/2011 | Stubbs ..................... A61N 1/37 |
| | | | 324/318 |
| 2012/0268124 | A1* | 10/2012 | Herbst ............. G01R 33/56509 |
| | | | 324/309 |
| 2014/0327438 | A1 | 11/2014 | Barmet et al. |
| 2015/0287189 | A1* | 10/2015 | Hirai ....................... G06T 19/20 |
| | | | 600/1 |
| 2016/0003929 | A1* | 1/2016 | Popescu ............... G01R 33/482 |
| | | | 324/322 |
| 2016/0035108 | A1* | 2/2016 | Yu .......................... A61B 5/721 |
| | | | 382/131 |
| 2018/0128889 | A1* | 5/2018 | Gross .................. G01R 33/389 |
| 2018/0231622 | A1* | 8/2018 | Hetz ....................... A61B 5/055 |
| 2018/0335495 | A1* | 11/2018 | Stainsby .......... G01R 33/56572 |
| 2019/0025397 | A1* | 1/2019 | Harris ............. G01R 33/56518 |
| 2020/0237334 | A1* | 7/2020 | Koken ................. A61B 5/1079 |
| 2020/0300945 | A1 | 9/2020 | Roy-Guay |
| 2021/0386347 | A1* | 12/2021 | Moriya ................. G01R 33/26 |
| 2021/0405136 | A1 | 12/2021 | Arroyo Camejo et al. |
| 2022/0018912 | A1* | 1/2022 | Popescu ............... G01R 33/24 |
| 2022/0202499 | A1* | 6/2022 | Zhang ..................... A61B 34/20 |
| 2022/0229130 | A1* | 7/2022 | Hattaha ................ G01R 33/385 |
| 2022/0378391 | A1* | 12/2022 | Suehling .............. G01R 33/283 |
| 2022/0386873 | A1* | 12/2022 | Oida ..................... A61B 5/0042 |

FOREIGN PATENT DOCUMENTS

| EP | 1582886 A1 | 10/2005 |
| WO | 2019174975 A1 | 9/2019 |

OTHER PUBLICATIONS

Bevelacqua, Peter Joseph; "Magnetic Field Boundary Conditions," https://www.antenna-theory.com/tutorial/electromagnetics/magnetic-field-boundary-conditions.php.
Skope "Dynamic Field Camera—The oscilloscope for MRI" http://www.skope.swiss/dynamic-field-camera/, Jul. 9, 2018.
Bernstein, Matt A. et al. "Concomitant Gradient Terms in Phase Contrast MR: Analysis and Correction" Magnetic Resonance in Medicine, vol. 39, No. 2, pp. 300-308, 1998.

* cited by examiner

MAGNETIC RESONANCE IMAGING DEVICE, COMPUTER-IMPLEMENTED METHOD FOR OPERATING A MAGNETIC RESONANCE IMAGING DEVICE, COMPUTER PROGRAM AND ELECTRONICALLY READABLE STORAGE MEDIUM

CROSS REFERENCE TO RELATED APPLICATIONS

This patent application claims priority to European Patent Application No. 21155850.7, filed Feb. 8, 2021, which is incorporated herein by reference in its entirety.

BACKGROUND

Field

The disclosure concerns a magnetic resonance imaging device, a computer-implemented method for operating a magnetic resonance imaging device, a computer program and an electronically readable storage medium configured to provide an improved approach for better correction of the effects of imperfections of the magnetic field in the imaging regions in magnetic resonance imaging.

Related Art

Magnetic resonance imaging (MRI) has become an established modality, in particular in medical imaging applications. A subject to be imaged is introduced into a main magnetic field (B0 field or static field), which leads to alignment of spins within the subject. The main magnetic field is usually generated by a main field unit, which may comprise a superconducting coil. The main field unit may include a substantially cylindrical bore surrounded by the superconducting coil/magnet, into which the subject to be imaged may be introduced, for example on a movable patient table. The magnetic resonance imaging device further comprises a radio frequency assembly having at least one radio frequency coil for emitting radio frequency signals, in particular excitation signals, into the imaging region. This causes the spins to process, wherein the decay of this excitation can be measured by at least one of the at least one radio frequency coils as the magnetic resonance signal. Spatial encoding is provided by the gradient fields of a gradient coil assembly, as in principle known in the art. The gradient fields spatially modify the main magnetic field.

It should be noted at this point that, in principle, the field of view of a magnetic resonance imaging device is usually defined as a homogeneity volume in which the main magnetic field does not exceed an allowed deviation from a nominal value, for example 1.5 or 3 Tesla. The actual imaging region, for example in an imaging process of a region of interest, may, however, only be a subvolume of the field of view. In particular, local coils, that is local radio frequency transmission or reception coils, have been proposed and used for, for example, imaging the head and/or neck region and/or extremities of the patient. However, of course, the imaging region may also comprise the whole field of view in some cases.

A prerequisite for a perfect magnetic resonance imaging process would require perfect magnetic field conditions in the imaging region. In particular, such ideal prerequisites concern both the fields for signal generation, in particular the main magnetic field (B0 field), and the fields for spatial signal encoding, that is the dynamic field gradients, usually Gx, Gy and Gz. The strength of the magnetic field in the imaging region is assumed to have a uniform distribution with a precision of less than a few ppm. Moreover, the magnetic field lines should be perfectly straight (linear) and parallel, that is, the main magnetic field B0 is oriented along a certain predefined direction, for example the z direction, with B0=B0z and no transverse components (B0x=B0y=0). The magnetic field gradients used for spatial signal encoding should also be oriented along this z axis being used to vary the strength of B0z linearly proportional to the local coordinates (x,y,z), that is, $Bz(x,y,z)=B0+GX*x+GY*y+GZ*z$, and further $Bx(x,y,z)=By(x,y,z)=0$. These equations can be understood as defining an ideal reference field. Usually, in a cylindrical magnetic resonance device, the z direction is defined as the longitudinal direction of the bore and the nominal direction of the main magnetic field.

However, in practice, the magnetic fields used for imaging in magnetic resonance imaging devices deviate from the idealized assumptions, in particular the reference field, described above, such that measurement errors, for example as imaging artifacts, may occur if the deviations are too strong. The deviations and resulting problems in the imaging process may be classified in three major groups:

a) Main magnetic field inhomogeneities, that is static or very-low frequency (less than 1 Hz) variations of the main field distribution over the imaging volume. The main field strength may drift due to thermal effects caused by temperature variations and/or floor borne or other mechanic vibrations with deformations of the main magnet parts, of the main magnetic field generating, in particular superconducting, coils, of cold shields as well as of an outer vacuum enclosure within a superconducting magnet. External sources may also alter the distribution of main magnetic field. These may be elevators transporting medical staff or patients within hospital buildings or other massive ferromagnetic objects moving within the stray field of a magnetic resonance imaging device.

b) Susceptibility effects, which comprise low-frequency (less than 100 Hz) varying inhomogeneities in main field distribution over the imaging region. These effects are produced, for example, by magnetic susceptibility changes occurring when the subject, in particular the patient body, enters the imaging region. These distortions further fluctuate due to patient motion or periodic motion of body parts related to, for example, respiration and/or cardiac activity.

c) Dynamic field distortions, which is mid-frequency (up to 10 kHz) variations in the gradient fields used for the spatial encoding of the magnetic resonance signals. These errors are due to gradient non-linearities inducing high-order terms, cross-term products and concomitant or unavoidable Maxwell terms. Additionally, parasitic eddy currents induced into electrically conducting scanner components or into the patient body generate substantial deviations away from the ideal encoding gradients.

All these imperfections lead to specific image artefacts and thus they require implementing various detection and correction countermeasures. Uncorrected or not fully corrected errors regarding the magnetic fields are the biggest impediment obstructing the vision of quantitative imaging in magnetic resonance imaging.

Hence, various methods to detect and correct magnetic field errors in magnetic resonance imaging have been proposed in the art. Most of these approaches at least partially account for only one or a few, but not all, of the imperfections mentioned above. For example, a main field drift may be corrected by repeated recalibration of the central frequency (Larmor frequency) f0. To correct for susceptibility artefacts, a time-consuming mapping of the main magnetic field before the imaging scan is performed and shim currents in the gradient coil assembly are adjusted to at least partially compensate the main field distortions across the imaging region.

Recently, an advanced approach has been proposed to address all technical problems regarding the magnetic field listed above. This approach uses a so-called "Dynamic Field Camera" (DFC), for example commercially available from Skope Magnetic Resonance Technologies AG, Zurich, Switzerland. Such a field camera uses multiple active magnetic field sensors (probes) to sample the magnetic field strength at a certain number of measurement positions, which may be spread across a sphere that encloses the imaging region. By using the Helmholtz theorem and applying a decomposition of the magnetic field using scalar spherical harmonics, it becomes possible to calculate the value of the magnetic field at any point enclosed by the measurement positions. By repeating this process periodically in time such a DFC is also able to track dynamic changes in the magnetic field distribution with high accuracy. Exemplarily, it is referred to U.S. Pat. No. 9,791,526 B2 describing such dynamic field camera arrangement.

There are two possible modes of operation:

a) In a first mode, the DFC is positioned within the field of view without an imaging subject (off-line). This pre-calibration mode quantifies the static main field inhomogeneities as well as the gradient errors by measuring gradient fields generated using well-defined gradient pulse waveforms. This allows to calculate the Gradient Impulse Response Functions (GIRFs), which may be used at a later time during imaging to correct or compensate for gradient field errors.

b) In a second mode the DFC magnetic field sensors surround the ROI of an imaging subject with the magnetic field sensors dynamically acquiring sensor data describing the magnetic field in the imaging region, including errors that occur during the scan (on-line). Measurable imperfections of the magnetic field thus include the drift effects as well as the subject-dependent effects.

It is noted that a special off-line field camera, which may be referred to as a "shim device," is used as a service tool for shimming a new magnet after production or after installation at the site of operation, for example, as described in U.S. Pat. No. 5,055,791 A or U.S. Pat. No. 10,018,690 B2.

Hence, a field camera used for pre-calibration as well as real-time magnetic field measurements provided by the dynamic field camera can be used to correct for the main magnetic field drift, the low-frequency magnetic field distortions and for errors induced by inaccurate gradient waveforms. For example, resulting magnetic field information can be used in a later model-based image reconstruction step to correct for the detected field errors. However, there have been studies showing that, despite these claimed capabilities, the image artefacts are not fully eliminated when using such a field camera. Hence, image artefacts due to magnetic field imperfections still occur.

BRIEF DESCRIPTION OF THE DRAWINGS/FIGURES

The accompanying drawings, which are incorporated herein and form a part of the specification, illustrate the embodiments of the present disclosure and, together with the description, further serve to explain the principles of the embodiments and to enable a person skilled in the pertinent art to make and use the embodiments.

FIG. 1 a flow chart of a method according to an exemplary embodiment of the disclosure.

Figure 2:
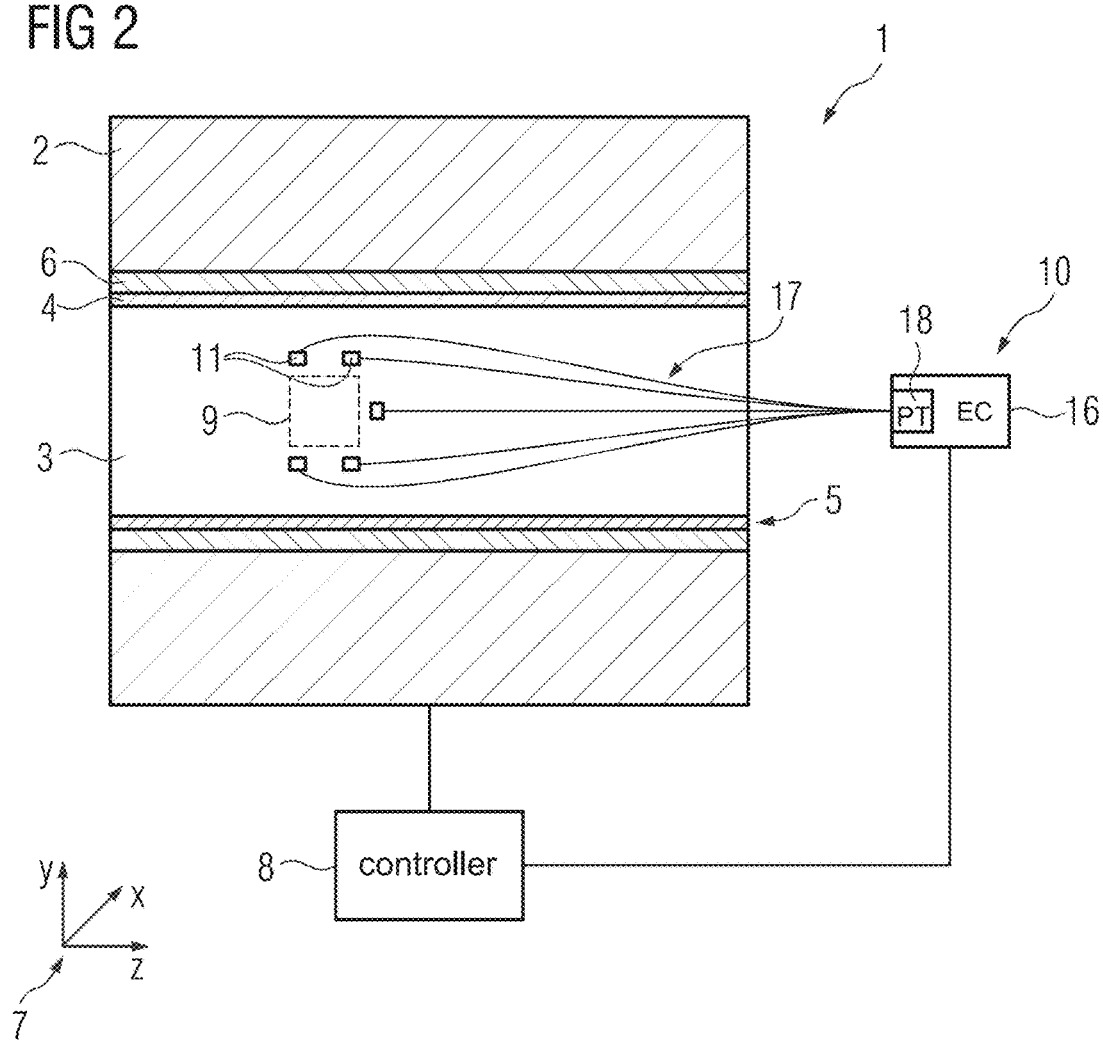

FIG. 2 a magnetic resonance imaging device according to an exemplary embodiment of the disclosure.

Figure 3:
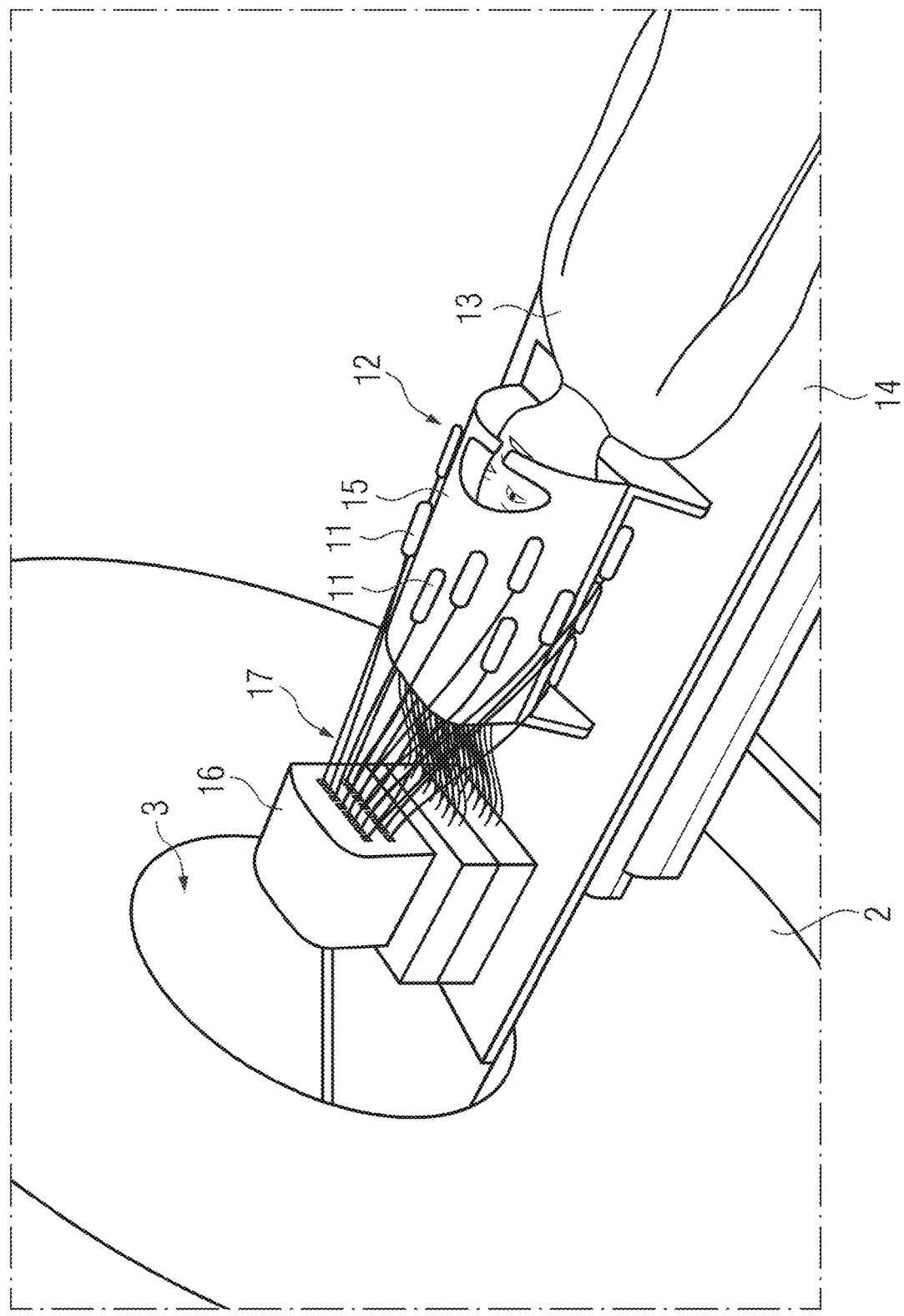

FIG. 3 a local coil according to an exemplary embodiment of the disclosure.

Figure 4:
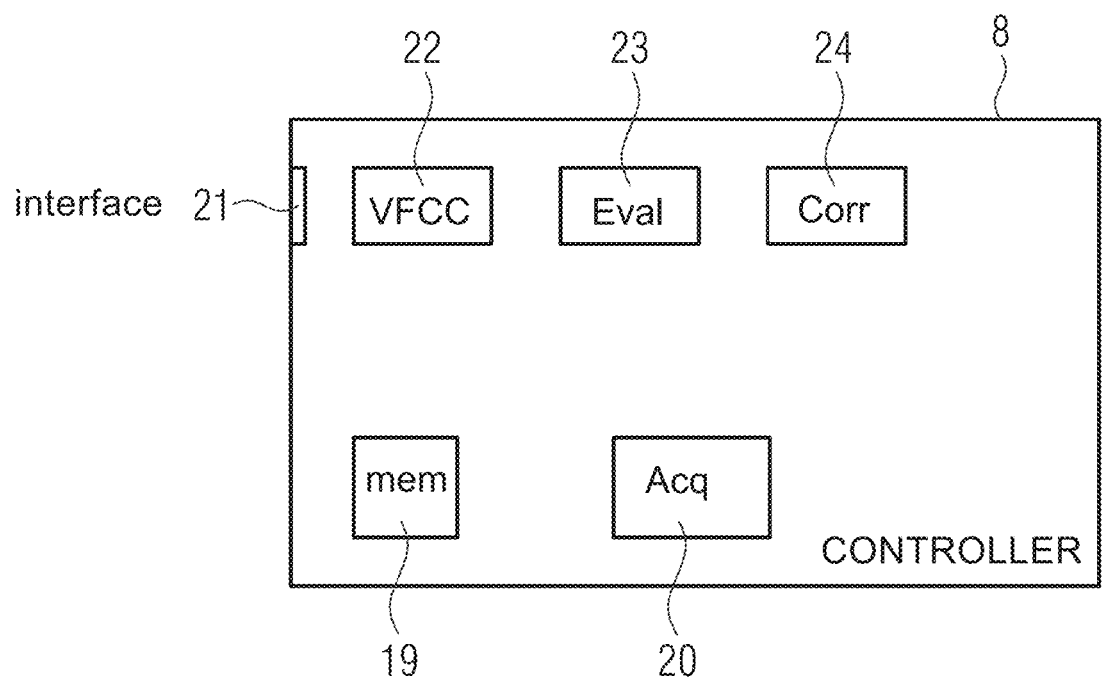

FIG. 4 shows the functional structure of a controller of the magnetic resonance imaging device according to an exemplary embodiment of the disclosure.

The exemplary embodiments of the present disclosure will be described with reference to the accompanying drawings. Elements, features and components that are identical, functionally identical and have the same effect are—insofar as is not stated otherwise—respectively provided with the same reference character.

DETAILED DESCRIPTION

In the following description, numerous specific details are set forth in order to provide a thorough understanding of the embodiments of the present disclosure. However, it will be apparent to those skilled in the art that the embodiments, including structures, systems, and methods, may be practiced without these specific details. The description and representation herein are the common means used by those experienced or skilled in the art to most effectively convey the substance of their work to others skilled in the art. In other instances, well-known methods, procedures, components, and circuitry have not been described in detail to avoid unnecessarily obscuring embodiments of the disclosure. The connections shown in the figures between functional units or other elements can also be implemented as indirect connections, wherein a connection can be wireless or wired. Functional units can be implemented as hardware, software or a combination of hardware and software.

It is an object of the current disclosure to provide an improved approach for better correction of the effects of imperfections of the magnetic field in the imaging regions in magnetic resonance imaging.

This object is achieved by providing a magnetic resonance imaging device, a computer-implemented method for operating a magnetic resonance imaging device, a computer program and an electronically readable storage medium according to exemplary embodiments.

A magnetic resonance imaging device may include a main field unit for establishing a main magnetic field in an imaging region, a gradient coil assembly for generating a gradient field in the imaging region, a radio frequency assembly for sending excitation signals to and receiving magnetic resonance signals from the imaging region, and at least one field camera for determining magnetic field information in the imaging region. The field camera may include multiple magnetic field sensors arranged at predefined measurement positions enclosing the imaging region, and a controller. The controller may be configured to: receive sensor data for each of the predefined measurement positions, from the sensor data, calculate the magnetic field information for the imaging region, and implement at least one calibration and/or correction measure depending on the magnetic field information.

In a magnetic resonance imaging device as initially described, according to the disclosure, the field camera is a vector field camera acquiring vector-valued sensor data describing the magnetic field at each measurement positions three-dimensionally, and the controller is configured to determine the magnetic field information to three dimensionally describe the magnetic field in the imaging region.

In the course of the current disclosure, it was found that the problem resulting in insufficient correction measures in the conventional field cameras was that their magnetic field sensors only measured the scalar value (i.e. the magnitude) of the magnetic field at their respective measurement positions. This is, as will be shown in detail below, a major shortcoming of the conventional approaches, which explains the limitations and residual errors of such devices.

Magnetic field sensors of conventional field cameras can only sense the local amplitude of the magnetic field vector, but not its orientation at the measurement position. Hence, the conventional field camera is in fact a scalar field camera (SFC) that samples a spatial distribution of the magnetic field amplitude B. It is noted that this absolute value is a scalar function whilst the real magnetic field is a vector field with the magnetic field vector having, in practice, a slightly different orientation at each spatial location. A well-known consequence of the physics laws expressed by the Maxwell equations is that the magnetic field lines follow closed contours. Therefore, within any field region the magnetic field lines have a non-zero curvature. As the magnetic field vector is tangent to a magnetic field line at every point, this non-zero curvature forces the magnetic field vector to change its orientation following the local curvature.

In general, the scalar amplitude of a Laplacian vector field, that is, a vector field distribution that obeys the Laplace equation, is not necessarily a Laplacian function. This may be true in some cases, for example when the vector field has zero curvature at any point. However, the conventional field cameras and the evaluation of their sensor data rely on a spatial modelling and decomposition of the magnetic field distribution which is based on scalar spherical harmonics. This would be correct only if the scalar magnetic field distribution was a Laplacian function, for example with $Bx=By=0$. In conclusion, the conventional field camera relies on the same assumption made by the traditional magnetic resonance imaging process, namely that the magnetic field has an ideal distribution along straight axial lines across the whole imaging region and the encoding gradients including the non-ideal terms add scalarly (algebraically) to the basic magnetic field. Generally, this assumption is incorrect, as will be shown by the facts listed below:

The main field unit generates a spatial distribution for the main magnetic field vector that is not precisely oriented along the z direction. The conventional field camera described above only observes the scalar Bz component while ignoring all other components.

The orientation of the magnetic field vector changes at the interfaces between air and tissue (or other materials) due to unmatched magnetic susceptibility. Depending on tissue conductivity the component of the magnetic field vector tangential to the separation surface will change due to induced surface currents. Combined with patient motion, for example due to respiration, these effects become even worse.

The magnetic gradient fields, as generated by the gradient coil, include unwanted field components orthogonal to the z direction, also known as concomitant terms or as unavoidable Maxwell terms. These components are known in the art to lead to image artefacts.

In particular the eddy currents induced by the gradient pulses into electrically conducting components, but also other effects, generate magnetic field vectors not only along the z direction, since they may concern any direction. Thus, the magnetic field is distorted by strong non-z components.

These problems become even more acute for dedicated magnetic resonance imaging devices or special gradient coil assemblies like, for example, small-bore scanners for head only MRI or dental MRI, or devices comprising open magnets with non-cylindrical geometries, like V-shaped, planar, or asymmetric dipolar magnets.

The worst consequences for magnetic resonance imaging result at low field ($B0=0.5$ T or less), when relatively strong gradients are used, for example for diffusion imaging. Here, the gradient field errors scale with the squared gradient amplitude as the ratio between the concomitant fields and magnetic field amplitude increases.

In summary, conventional field cameras use magnetic field sensors that are insensitive to the magnetic field orientation. Consequently, the conventional approaches assume that the magnetic vector field is precisely oriented along the z axis and performs the magnetic field modelling based on this assumption, thus delivering erroneous results as this approximation is not sufficiently correct. The algorithmic method used to decompose and model the spatial distribution of the magnetic field makes use of scalar spherical harmonics that are not able to handle vector fields. Furthermore, the conventional methods used to correct the field errors also assume that those errors are only affecting the z component of the magnetic field and are thus unable to deal with non-z error terms.

As contrasted with the conventional approaches using magnetic field sensors that are insensitive to the magnetic field orientation, the current disclosure uses a vector field camera (VFC) using magnetic field sensors also measuring the orientation of the magnetic field, which replace the magnetic field probes of the conventional approaches providing only the magnitude. In other words, the magnetic field sensors of the disclosure, which may also be termed vector magnetometers, provide both magnitude and orientation of the magnetic field at their measurement position, hence the complete magnetic field vector. The orientation information is taken into account when implementing calibration and/or correction measures, thus greatly improving their quality and providing better imaging quality with less artifacts.

In particular, a correction measure may be implemented if the magnetic field information indicates a deviation of the magnetic field from a reference field in the imaging region fulfilling a correction criterion. In an exemplary embodiment, the reference field may also be provided as a vector and may be defined as discussed above, namely as the nominal, homogeneous main magnetic field in the nominal direction, which is preferably also the z direction, including, if applicable, the gradients. As further discussed below, deviations may also be evaluated over time if multiple measurements are taken spaced apart in time. Correction criteria may evaluate the momentaneous magnetic field according to the magnetic field information, but also its evolution over time, in particular for a time series of magnetic field information.

In exemplary embodiments, the magnetic field sensors of the vector field camera comprise at least one magnetometer measuring optically detected magnetic resonance (ODMR) spectra and/or at least one Hall effect sensor modified for three-dimensional sensing. For example, U.S. Pat. No. 6,800,913 B2 discloses a modified Hall effect device capable of measuring the individual components of a magnetic vector field which can also be employed in the current disclosure. However, in an exemplary embodiment, the ODMR-based vector magnetometers featuring optical excitation and optical readout are employed, since they provide better compatibility with the magnetic resonance imaging environment. Corresponding technology is, for example, disclosed in US 2020/0300945 A1 and DE 10 2018 203 845 A1. For example, ODMR spectra of Nitrogen-Vacancy pair Centers (NVC) in diamond may be detected. Both the Hall technology and the ODMR technology allow for a high degree of integration on extremely small silicon chips or diamond crystals, respectively.

In an exemplary embodiment, in particular for magnetometers measuring optically detected magnetic resonance spectra, the vector field camera may comprise optical signal lines for each magnetic field sensor and/or may comprise, for the magnetic field sensors, a power transmission device, working at a frequency of at least 1 GHz and/or not being a harmonic of the Larmor frequency of the magnetic resonance imaging device, and/or using dielectric waveguides as power transmission lines. In this manner, additional problems regarding known field cameras of the state of the art may additionally be solved using the current disclosure. Conventional field cameras usually comprise coaxial radio frequency cables to connect electronic components to the magnetic field sensors. These cables are subject to standing waves that occur during transmission of high radio frequency power from the radio frequency assembly. They may lead to local wire heating resulting, for example, in discomfort for the patient and/or an operator. In particular when using ODMR sensors, the current disclosure allows to employ optical signal lines to transmit excitation light to the magnetic field sensor and to collect fluorescence light from the magnetic field sensor. Optical signal transmission leads to strongly decreased interference effects in MRI. In an exemplary embodiment, alternatively or additionally, power may be transmitted as microwave power using dielectric waveguides, for example at frequencies of 1 GHz or higher. Such power transmission also does not disturb the radio frequency fields used in MRI (whose frequencies lie in the MHz range) or the switched gradient fields in MRI (in the kHz range), since in those frequency ranges, dielectric waveguides behave like insulators. Hence, they are invisible to the gradient fields and radio frequency fields of the imaging process.

In particular, high frequency excitation signals for ODMR sensors, which provide excitation for the optically detectable magnetic resonance effect, have frequencies in the GHz range and may also use dielectric waveguides, while illumination light and fluorescence signals may be guided in optical signal lines. For a Hall sensor, on the other hand, operating power for performing measurements may be provided via dielectric waveguides at frequencies larger than 1 GHz.

In further exemplary embodiments, at least one electronic component of the vector field camera and/or the controller is positioned at least partly at least a predetermined distance away from the imaging region and/or outside a bore of the magnetic resonance imaging device and/or a shielded room of the magnetic resonance imaging device. That is, by choosing the length of wire of the vector field camera, in particular optical signal lines and/or dielectric waveguides as discussed above, accordingly, electronic components, for example for evaluation of raw data from the magnetic field sensors, may be positioned far away from the scanner itself, in particular outside of the bore or even outside the shielded room. In this manner, radio frequency noise emitted from such electronic components can be reduced or even omitted, such that the imaging process is not interfered with, in particular regarding radio frequency coils of the radio frequency assembly.

In embodiments, the magnetic field sensors may be positioned such that the measurement positions lie on a certain, predefined surface, in particular a sphere enclosing the imaging region.

In an exemplary embodiment, the vector field camera may be designed based on at least one assumption, in particular that the sign of the projection of the magnetic field vector onto a nominal direction of the main magnetic field does not change in the imaging region, regarding the magnetic field and/or the controller is adapted to determine the magnetic field information based on the at least one assumption. Magnetic resonance imaging uses a strong main magnetic field along a nominal direction, here called the z direction. Hence, it is possible to assume that that the direction of the magnetic field vectors does not change over the imaging region. In concrete terms, this assumption can be formulated in that the projection of the magnetic field vector onto the nominal direction (which usually is the z axis and/or the rotational symmetry axis of the bore/the main field generating magnet) is always positive or is always negative (depending on the convention used for the coordinate system of reference). In other words, the sign of this component of the magnetic field vector does not change. This observation substantially simplifies the construction, the calibration and the operation of the vector magnetometers, that is, the magnetic field sensors of the vector field camera. For example, if the magnetic field vectors are designed to measure projections of the magnetic field vector onto certain axes, it is very complicated to determine the actual sign of the projection. Using the above discussed assumption, complex measures to determine the sign of the projection for at least the z axis are not required, since it should not change over the imaging region and is known in advance, leading to a simplified design of the magnetic field sensors.

The vector field camera of the disclosure is configured and designed to sample the three-dimensional distribution of the vector magnetic field at predefined spatial measurement locations enclosing the imaging region. In principle, the vector field camera described here may be used, for example in calibration processes, to perform a static magnetic field measurement, in particular with no imaging subject present in the field of view, such that the main magnetic field (B0 field) can be measured. However, in exemplary embodiments, the controller is configured to control the vector field camera to periodically acquire sensor data to determine dynamic magnetic field information. In this case, a dynamic vector field camera (DVFC) results. Dynamic perturbations or generally variations of the magnetic field may, in this manner, also be measured, for example regarding effects in groups b) and c) as initially described. In particular, measurements may be taken at least essentially in real-time, since in particular the above-mentioned magnetic field sensors of the vector field camera allow very fast measurements and hence high sampling frequency. For example, to measure dynamic field distortions up to 10 kHz, the temporal sampling frequency may be chosen in the interval of 20 kHz to 1000 kHz, in particular 50 to 100 kHz.

In an exemplary embodiment, the magnetic field information allows determining magnetic field strengths and orientations at arbitrary positions inside the imaging region. Hence, in an exemplary embodiment, to determine the magnetic field information for at least the imaging region from the samples taken at a few measurement positions, the vector magnetic field is modelled and the model is fitted to the actual sensor data.

In exemplary embodiments, the controller may be configured, for determining the magnetic field information, to fit the parameters of a magnetic field model to the sensor data at all measurement positions, wherein the magnetic field model comprises a series decomposition of the vector-valued magnetic field regarding, in particular orthogonal, vector-valued basis functions. Comparable to scalar functions, for which a series expansion using scalar basis functions is possible (and employed for conventional scalar field cameras), a series expansion using vector basis functions can be employed to model the vector magnetic field. Using the measured magnetic field values in the sensor data, the coefficients of the series expansion are optimized such that the model becomes a best fit for the actual magnetic field. Once the coefficients of the magnetic field model are known, that is, the magnetic field model has been fitted, it becomes possible to evaluate the magnetic field at any arbitrary location.

In an exemplary embodiment, the controller is configured to use, in particular real-valued, vector spherical harmonics as the basis functions and/or the series decomposition comprises at least terms of up to second order, in particular up to third order. Since the main magnetic field is a Laplacian field obeying the Laplace equation, Vector Spherical Harmonics (VSH) are a good candidate for the vector basis functions. The orthogonal VSH already have wide applications in geophysics, quantum mechanics and astrophysics. Consequently, a large pool of suitable yet easily available software tools, libraries and open source code may be used to implement this embodiment. VSH are, for example, available in the software package MATLAB by MathWorks Corporation, Natick, Mass., USA, and the software package Mathematica from Wolfram Research Inc., Champaign, Ill., USA.

It is noted that there are several versions of VSH with different notation and properties being used in practice. In an exemplary embodiment, the VHS may be constructed by applying the gradient operator $\nabla$ to the well-known scalar spherical harmonics—SSH. Expressed in spherical coordinates and for each SSH $Y_{lm}(r, \theta, \varphi)$, three orthogonal vector spherical harmonics Y, $\Psi$ and $\Phi$, in their mathematical expressions:

$$Y_{lm} = Y_{lm}\hat{r}$$

$$\Psi_{lm} = r\nabla Y_{lm}$$

$$\Phi_{lm} = r \times \nabla Y_{lm} \quad (1)$$

may be defined, with $\nabla = \hat{\theta}\partial_\theta + \hat{\Phi}(\sin\theta)^{-1}\partial_\varphi$. These VSH have the following conjugate symmetry:

$$\{Y, \Psi, \Phi\}_{l,-m} = (-1)^m \{Y, \Psi, \Phi\}_{lm}^* \quad (2)$$

The indexes l, m are the orbital numbers as known from the art for indexing and ordering the spherical harmonics.

As the vector magnetic field to be described is a real-valued vector field, using complex-valued VSH would lead to unnecessary redundancy in the number of basis functions and fitting coefficients, and the expansion for the magnetic field must be real-valued. Thus, in an exemplary embodiment, real-valued vector spherical harmonics are used. The real-valued VSH may be simply derived from the complex-valued VSH. The basic principle is that any linear combination of the initial complex VSH will still be an eigenfunction or solution of the field equation. Further observing the conjugate symmetry of the VSH as shown in formula (2), the real-valued VSH functions can by chosen by combining the complex conjugate VSH pairs, for example by adding and subtracting the ones corresponding to opposite values of m. These algebraic operations providing, respectively, a pure real and a pure imaginary result are completed by discharging the factor i in the imaginary result. It is noted that all VSH corresponding to m=0 are already real-valued. Such a definition of real-valued VSH is well known in the state of the art. As an example, it is referred to an article by M. A. Blanco et al., "Evaluation of rotation matrices in the basis of real spherical harmonics", Journal of Molecular Structure (Theochem) 419 (1997), pages 19-27.

Despite their name, spherical harmonics take their simplest form in Cartesian coordinates, where they can be expressed as homogeneous polynomials of degree 1 in (x,y,z) that obey the Laplace equation. In an exemplary embodiment, VSH expressed in Cartesian coordinates are used, such that, advantageously, their numerical evaluation is simplified and accelerated. It is noted that known and commercially available software packages provide a library of functions for transformation of coordinates.

In an exemplary embodiment of the disclosure, real-valued VSH expressed in Cartesian coordinates are used. However, the method disclosed below applies as well for any other VSH variant. The vector magnetic field B may be modeled by a weighted average of real-valued VSH up to the necessary degree of extension N as $$B(r) = \sum_{i=1}^{N} c_i \cdot VSH_i(r). \quad (3)$$

In the expression above the number of expansion terms N gives the accuracy of the magnetic field model. A higher N guarantees a better accuracy, yet with the disadvantage of higher computational effort and the requirement for more magnetic field sensors. In practice, an appropriate value for N that fits the complexity of the magnetic field to be modelled and minimizes the cost of operation may be chosen. The real-valued coefficients $c_i$ are the model parameters that have to be optimized to achieve the best accuracy during the model fitting. The position vector r denotes the spatial location of the point where at the magnetic field is to be determined. It can be expressed in Cartesian coordinates as (x, y, z), spherical coordinates as (r, $\theta$, $\varphi$), etc. The vector basis functions $VSH_i$ with i=1 . . . N will be selected according to the table below by following the sub-indexes of increasing orbital numbers

| Orbital numbers | VHS | Number of VHS |
| --- | --- | --- |
| l = 0, m = 0 | $Y_{00}$ | 1 |
| l = 1, −1 ≤ m ≤ 1 | $Y_{1,-1}\ Y_{10}\ Y_{11}$ | 9 |
| | $\Psi_{1,-1}\ \Psi_{10}\ \Psi_{11}$ | |
| | $\Phi_{1,-1}\ \Phi_{10}\ \Phi_{11}$ | |
| l = 2, −2 ≤ m ≤ 2 | $Y_{2,-2}\ Y_{2,-1}\ Y_{20}\ Y_{21}\ Y_{22}$ | 15 |
| | $\Psi_{2,-2}\ \Psi_{2,-1}\ \Psi_{20}\ \Psi_{21}\ \Psi_{22}$ | |
| | $\Phi_{2,-2}\ \Phi_{2,-1}\ \Phi_{20}\ \Phi_{21}\ \Phi_{22}$ | |
| . . . | . . . | . . . |

For example, a magnetic field decomposition including all expansion terms up to the second order uses the first 25 VSH functions listed in the table above for l=0, 1 and 2. It also means that this magnetic field model features, as modelling parameters, N=25 expansion coefficients $c_i$ that need to be fitted. A more accurate field model including expansion terms up to the third order l=3 requires N=46 expansion coefficients $c_i$, since the third order adds 21 VHS.

The magnetic field model is fitted to the real magnetic field distribution described by the sensor data. That is, the expansion coefficients $c_i$ are adjusted to best approximate all measured values of the vector magnetic field at the measurement positions. In an exemplary embodiment, the number of magnetic field sensors is at least equal to the number of basis functions used in the series decomposition. For a total number of M magnetic field sensors located at the measurement positions $r_j$ and considering a static case, the sensor data provided by the magnetic field sensors are the field vectors $B(r_j)$. The field model defined in (3) allows writing the following equation for any $j=1 \ldots M$:

$$B(r_j) = \sum_{i=1}^{N} c_i \cdot VSH_i(r_j) \quad (4)$$

Thus, a total of M equations for N unknowns $c_i$ exist. If $M \geq N$, this system of equations is determined or even overdetermined. Various methods are known in the art to solve such a system of equations and to determine the field model, which can also be applied in the current disclosure. For example, the method of ordinary least squares can be used to find the solution to overdetermined systems.

If sensor data are recorded at multiple time points $t_k$, that is, dynamic vector magnetic fields with non-stationary time evolution are to be evaluated, the system of equations $$B(r_j, t_k) = \sum_{i=1}^{N} c_i(t_k) \cdot VSH_i(r_j) \quad (5)$$

can be solved separately for all time slots $t_k$. In this dynamic case the model parameters $c_i$ may differ for different time points.

Although this embodiment has been described very exhaustively, the scope of the disclosure is not limited to the disclosed examples. In practice, any other vector field decomposition method and modelling approach can be used. For example, the magnetic vector field may be decomposed into a divergence-free component, a rotation-free component and a harmonic component, or the Helmholtz-Hodge decomposition on a sphere could be employed. In is also possible to use generalized vector field decompositions into a gradient and a Hamiltonian vector field.

Regarding calibration or correction measures, many steps already known from the state of the art are conceivable, wherein they may have to be adapted to the use of vector magnetic fields, which, in most cases, is trivial to achieve.

In embodiments, for example, the controller may be configured to detect, as at least one deviation, an inhomogeneity of the magnetic field, wherein at least one shimming device is controlled to at least partly compensate the inhomogeneity. For example, shimming devices comprising shim coils have been proposed in the state of the art, whose field characteristics for different currents are well-known. Currents can now be chosen for the shim coils such that the shim field generated by the shim coils at least essentially compensates the inhomogeneities.

If dynamic measurements are performed, the magnetic field information does not only describe the inherent inhomogeneities of the main magnetic field, but also characterise the drift of the basic field as well as the non-idealities of the pulsing gradient fields. In an exemplary embodiment of the disclosure, the controller is adapted to, for at least one gradient axis, determine a vector gradient impulse response function (VGIRF) by controlling the gradient coil arrangement to apply a predefined gradient pulse for the imaging region,
simultaneously to outputting the predefined gradient pulse, controlling the vector field camera to determine dynamic sensor data at the measurement positions, and
determining the vector gradient impulse response function from dynamic magnetic field information determined from the dynamic sensor data.

Hence, the disclosure allows to calibrate VGRIFS for any gradient axis. At least one gradient coil of the gradient coil assembly is controlled according to a predefined gradient pulse, in particular driven by a predefined current waveform, for example a rectangular gradient pulse or a triangular shaped gradient pulse. Simultaneously, the impulse response as dynamic vector magnetic field evolutions is measured using the vector field camera, such that the corresponding dynamic magnetic field information may be determined. Once calibrated, the VGIRF allows estimating the gradient fields resulting from driving the gradient coil using an arbitrary current waveform I(t)

$$G_\delta(r, t) = VGIRF \otimes I_\delta(t). \quad (6)$$

Unlike the scalar assumption made by conventional approaches, the vector magnetic field within the imaging region results as a vector summation over all active vector gradients, given by:

$$B(r, t) = B_o(r) + \sum_{\delta = x, y, z} G_\delta(r, t)$$

It is noted that, after evaluating the distribution of the vector magnetic field in the imaging region as desired, the local amplitude of the field given by $B(r)=|B(r)|$ should be used to evaluate and/or to model the magnetic resonance signals. For example, the angular frequency of the magnetic resonance signal emerging at the spatial location r within the imaging region will be $\omega(r)=\gamma \cdot |B(r)|$, with $\gamma$ being the gyromagnetic constant for protons in water. This is because the magnetic resonance phenomenon is sensitive only to the local amplitude of the magnetic field, but not to its local orientation.

Of course, in embodiments, also correction measures correcting imperfections of the magnetic field during reconstruction of magnetic resonance data, for example images, from received magnetic resonance signals may be employed and may take advantage of the three-dimensional magnetic field information determined using the vector field camera.

In principle, the vector field camera of the disclosure may be designed to encompass a large portion of the field of view or even the whole field of view. Such a vector field camera may, for example, be used to calibrate off-line for the whole field of view. However, in concrete, exemplary embodiments, the vector field camera may be attached to and/or integrated into a local coil defining the imaging region.

In other words, according to an exemplary embodiment, the radio frequency arrangement comprises at least one local coil, in particular a head coil and/or an extremity coil, having a housing, wherein the magnetic field sensors are attached to and/or integrated into the housing. In an exemplary embodiment, the rigid housing defines a certain geometry of the local coil and usually surrounds and encloses the imaging region. The magnetic field sensors may thus be placed at predefined positions in or on the housing, in particular such that the measurement positions lie on a certain, predefined surface, in particular a sphere enclosing the imaging region. In this manner, a local coil also providing the capability to measure the vector magnetic field is realized.

A method according to the disclosure may be used to operate a magnetic resonance imaging device according to the disclosure. Hence, a computer-implemented method for operating a magnetic resonance imaging device, in particular a magnetic resonance imaging device according to the disclosure, to calibrate regarding the magnetic field and/or correct for magnetic field deviations, is provided, wherein the magnetic resonance imaging device comprises a main field unit for establishing a main magnetic field in an imaging region, a gradient coil assembly for generating a gradient field in the imaging region, a radio frequency assembly for sending excitation signals to and receiving magnetic resonance signals from the imaging region, at least one field camera for determining magnetic field information in the imaging region, the field camera comprising multiple magnetic field sensors arranged at predefined measurement positions enclosing the imaging region, and a controller. The method comprises the steps of receiving sensor data for each of the predefined measurement positions in the controller, from the sensor data, calculating the magnetic field information for the imaging region, in the controller and implementing, by the controller, at least one calibration and/or correction measure depending on the magnetic field information.

According to the disclosure, a vector field camera is used as the field camera, wherein vector-valued sensor data describing the magnetic field at the measurement positions three-dimensionally is acquired and the magnetic field information is determined to three dimensionally describe the magnetic field in the imaging region.

All features and remarks regarding the magnetic resonance imaging device according to the disclosure analogously apply to the method according to the disclosure, such that the same advantages can be achieved.

In an exemplary embodiment, the controller may comprise at least one processor and at least one memory. By hardware and/or software, functional units realizing the steps of the disclosure may be implemented. In particular, the controller may comprise a vector field camera controller for controlling the vector field camera to acquire sensor data, an evaluator to determine the magnetic field information from the sensor data, and a calibration and/or corrector for implementing the at least one calibration and/or correction measure. Further functional units may, of course, be provided to provide steps in exemplary embodiments. In an exemplary embodiment, the controller may also be configured to control imaging processes of the magnetic resonance imaging device and may thus also comprise an acquisition unit.

A computer program according to the disclosure is directly loadable into a memory of a controller of a magnetic resonance imaging device and comprises program means such that, when the computer program is executed on the controller, the steps of a method according to the disclosure are performed. The computer program may be stored on an electronically readable storage medium according to the disclosure, which thus has control information comprising at least a computer program according to the disclosure stored thereon, such that, when the storage medium is used in a controller of a magnetic resonance imaging device, the controller is caused to perform the steps of a method according to the disclosure. The electronically readable storage medium may be a non-transitional medium, for example a CD ROM.

FIG. 1 is a flowchart showing steps of a method according to the disclosure. In the method, magnetic field information regarding at least an imaging region in a magnetic resonance imaging device is determined using a field camera, such that the determined magnetic field information can be used for calibration and/or correction tasks. According to the disclosure, the magnetic field information describes the magnetic field in the imaging region three-dimensionally.

The method of FIG. 1 comprises three major steps S1, S2 and S3. In step S1, sensor data is acquired in a measurement using the field camera, which is a vector field camera. The vector field camera comprises multiple magnetic field sensors positioned at predetermined measurement positions, wherein the measurement positions enclose the imaging region. In particular, the measurement positions may be located on a surface enclosing the imaging region, for example a sphere. The magnetic field measurement sensors, which may also be called vector magnetometers, measure not only the magnitude of the magnetic field, but also its orientation, for example by measuring all components of a Cartesian magnetic field vector. While different types of magnetic field sensors may be employed, for example modified Hall-effect sensors, in this embodiment, the magnetic field sensors are ODMR sensors, which use optically detectable magnetic resonance (ODMR) as discussed above.

In a step S2, the sensor data of each measurement position are evaluated to determine three-dimensional, that is vector-valued, magnetic field information for the imaging region. That is, for arbitrary positions inside the imaging region, magnitude and orientation of the magnetic field may be determined from the magnetic field information. To achieve this, a magnetic field model is defined by performing a series expansion using vector basis functions. As the vector basis functions, preferably, real-valued vector spherical harmonics are used, as discussed above, but other approaches, in particular expansion methods, may also be used. The magnetic field model, which has, as model parameters, expansion coefficients for each of the vector basis functions, which in this case are orthogonal, is then fitted to the sensor data at the respective measurement positions. In particular, the number of magnetic field sensors may exceed the number of used vector basis functions and thus coefficients, such that an equation system can be formulated and solved, for example by the method of ordinary least squares.

It is noted that dynamic magnetic field information may be gathered by, in particular periodically, taking measurements at multiple time points in step S1. In this case, in an exemplary embodiment, the magnetic field information for each time point is separately determined and the magnetic field information for all points is then accumulated and provided as dynamic magnetic field information.

In a step S3, the magnetic field information is evaluated for at least one calibration and/or correction task. For example, vector gradient impulse response functions (VGIRF) may be determined as a calibration measure by controlling a gradient coil assembly of the magnetic resonance imaging device to output a predefined gradient pulse, during which the measurement in step S1 is performed. From the dynamic magnetic field information determined in step S2, the VGIRFs may be determined. In other applications, deviations from a reference field may be determined and corrected, for example by accordingly controlling a shimming device if a correction criterion is fulfilled. Furthermore, correction measures may be applied during reconstruction, for example of magnetic resonance images.

FIG. 2 is a schematical drawing of a magnetic resonance imaging device 1 according the disclosure. As in principle known, the magnetic resonance imaging device 1 comprises a main field unit 2 for generating the main magnetic field (B0 field), for example using a superconducting coil. The main field unit 2 is, in this case, essentially cylindrical and comprises a central, cylindrical bore 3 into which a patient may be introduced using a patient table (not shown in FIG. 2). Enclosing the bore 3 are a body coil 4, that is a radio frequency coil of a radio frequency assembly 5, and a gradient coil assembly 6 comprising gradient coils for three main directions of the magnetic imaging device 1. A respective coordinate system 7 is also shown in FIG. 2. The z-direction is the nominal direction of the main magnetic field and also the longitudinal direction of the bore 3. The x- and y-direction are the orthogonal, horizontal and vertical directions, as shown. Hence, the gradient coil assembly 6 may comprise a x-gradient coil, a y-gradient coil and a z-gradient coil.

The magnetic resonance imaging device 1 further comprises a controller 8 for controlling the operation of the magnetic resonance imaging device 1. The controller 8 is configured to perform a method according to the disclosure, that is, determine a three-dimensional magnetic field information for an imaging region 9 in the bore 3 and use it for correction and/or calibration tasks. To achieve this, the magnetic resonance imaging device 1 comprises a vector field camera 10 having multiple magnetic field sensors 11 (vector magnetometers), in this case ODMR sensors. The magnetic field sensors 11 are located at measurement positions enclosing the imaging region 9. For example, and as exemplarily shown in FIG. 3, they may be mounted to and/or integrated into a local coil 12, in this example a head coil for a patient 13 positioned on the patient table 14. The head coil 12 comprises a rigid housing 15, onto which the magnetic field sensors 11 are mounted.

As can be seen from FIGS. 2 and 3, the magnetic field sensors 12 are connected to an electronic component 16 of the vector field camera 10 via signal lines 17, in this case, optical signal lines 17. The optical signal lines 17 may, for example, comprise optical fibres that transmit excitation light and/or collect the fluorescence light from the magnetic field sensors 11, which are, as already explained, ODMR sensors. If electrical power and/or ODMR excitation signals are required in the magnetic field sensors 11, a power transmission device 18 only indicated in FIG. 2 may be used, which operates at power transmission frequencies larger than 1 GHZ and uses dielectric wave guides as power transmission lines, which are not shown for reasons of clarity. In particular, when using the ODMR sensors, excitation power in the microwave regime may be transmitted to the sample, for example diamond, using a dielectric waveguide and illumination light and fluorescence signals may be guided to electronic component 16 via optical signal lines 17. Regarding Hall sensors, in the alternative, the operating power may be provided by dielectric waveguides at frequencies larger than 1 GHz.

As shown at least in FIG. 2, the at least one electronic component may be positioned outside the bore 3 or even outside a shielded room of the magnetic resonance imaging device 1, since neither the optical signal lines 17 nor the electric wave guides interfere with the imaging process or considerably distort the magnetic field.

FIG. 4 shows the functional structure of the controller 8. The controller 8 comprises at least one memory 19, in which, for example, magnetic field information and/or sensor data may be stored. As the controller 8 also controls the operation of the magnetic resonance imaging device during imaging, it also comprises a respective acquisition unit 20.

The controller 8 further comprises an interface 21 to the vector field camera 10. Using the interface 21, the vector field camera 10 can be controlled and sensor data can be received.

A vector field camera controller 22 is provided to control the operation of the vector field camera 10 and receive sensor data via the interface 21, according to step S1 in FIG. 1. In an evaluator 23, the sensor data are evaluated to determine the magnetic field information according to step S2. The magnetic field information is provided to a calibration and/or corrector 24, such that calibration and/or correction measures can be executed as described with respect to step S3.

In an exemplary embodiment, the controller 8 includes processing circuitry that is configured to perform one or more functions and/or operations of the controller 8, including controlling the MRI device 1 and/or one or more components of the MRI device 1, processing magnetic resonance signals and/or other data, reconstructing magnetic resonance images, and/or one or more other operations of the controller 8. In an exemplary embodiment, one or more components of the controller 8 includes processing circuitry that is configured to perform one or more respective functions and/or operations of the component(s).

Although the present disclosure has been described in detail with reference to the exemplary embodiment, the present disclosure is not limited by the disclosed examples from which the skilled person is able to derive other variations without departing from the scope of the disclosure.

To enable those skilled in the art to better understand the solution of the present disclosure, the technical solution in the embodiments of the present disclosure is described clearly and completely below in conjunction with the drawings in the embodiments of the present disclosure. Obviously, the embodiments described are only some, not all, of the embodiments of the present disclosure. All other embodiments obtained by those skilled in the art on the basis of the embodiments in the present disclosure without any creative effort should fall within the scope of protection of the present disclosure.

It should be noted that the terms "first", "second", etc. in the description, claims and abovementioned drawings of the present disclosure are used to distinguish between similar objects, but not necessarily used to describe a specific order or sequence. It should be understood that data used in this way can be interchanged as appropriate so that the embodiments of the present disclosure described here can be implemented in an order other than those shown or described here. In addition, the terms "comprise" and "have" and any variants thereof are intended to cover non-exclusive inclusion. For example, a process, method, system, product or equipment comprising a series of steps or modules or units is not necessarily limited to those steps or modules or units which are clearly listed, but may comprise other steps or modules or units which are not clearly listed or are intrinsic to such processes, methods, products or equipment.

References in the specification to "one embodiment," "an embodiment," "an exemplary embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The exemplary embodiments described herein are provided for illustrative purposes, and are not limiting. Other exemplary embodiments are possible, and modifications may be made to the exemplary embodiments. Therefore, the specification is not meant to limit the disclosure. Rather, the scope of the disclosure is defined only in accordance with the following claims and their equivalents.

Embodiments may be implemented in hardware (e.g., circuits), firmware, software, or any combination thereof. Embodiments may also be implemented as instructions stored on a machine-readable medium, which may be read and executed by one or more processors. A machine-readable medium may include any mechanism for storing or transmitting information in a form readable by a machine (e.g., a computer). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others.

Further, firmware, software, routines, instructions may be described herein as performing certain actions. However, it should be appreciated that such descriptions are merely for convenience and that such actions in fact results from computing devices, processors, controllers, or other devices executing the firmware, software, routines, instructions, etc. Further, any of the implementation variations may be carried out by a general-purpose computer.

For the purposes of this discussion, the term "processing circuitry" shall be understood to be circuit(s) or processor(s), or a combination thereof. A circuit includes an analog circuit, a digital circuit, data processing circuit, other structural electronic hardware, or a combination thereof. A processor includes a microprocessor, a digital signal processor (DSP), central processor (CPU), application-specific instruction set processor (ASIP), graphics and/or image processor, multi-core processor, or other hardware processor. The processor may be "hard-coded" with instructions to perform corresponding function(s) according to aspects described herein. Alternatively, the processor may access an internal and/or external memory to retrieve instructions stored in the memory, which when executed by the processor, perform the corresponding function(s) associated with the processor, and/or one or more functions and/or operations related to the operation of a component having the processor included therein. In one or more of the exemplary embodiments described herein, the memory is any well-known volatile and/or non-volatile memory, including, for example, read-only memory (ROM), random access memory (RAM), flash memory, a magnetic storage media, an optical disc, erasable programmable read only memory (EPROM), and programmable read only memory (PROM). The memory can be non-removable, removable, or a combination of both.

The invention claimed is:

1. A magnetic resonance imaging (MRI) device, comprising:
   a main field unit configured to establish a main magnetic field in an imaging region;
   a gradient coil assembly configured to generate a gradient field in the imaging region;
   a radio frequency (RF) arrangement configured to send excitation signals to and receive magnetic resonance signals from the imaging region;
   a field camera configured to determine magnetic field information in the imaging region, the field camera including multiple magnetic field sensors arranged at predefined measurement positions enclosing the imaging region, the field camera being a vector field camera configured to acquire vector-valued sensor data describing the magnetic field at each of the measurement positions three-dimensionally, wherein the vector field camera comprises:
   for magnetometers measuring optically detected magnetic resonance spectra, optical signal lines for each magnetic field sensor, and/or
   for the magnetic field sensors, a power transmission device configured to work at a frequency of at least 1 GHz and/or not being a harmonic of the Larmor frequency of the magnetic resonance imaging device, and/or using dielectric waveguides as power transmission lines; and
   a controller configured to:
   receive sensor data for each of the predefined measurement positions,
   calculate the magnetic field information for the imaging region based on the sensor data to determine the magnetic field information to three dimensionally describe the magnetic field in the imaging region, and
   implement at least one calibration measure and/or correction measure based on the magnetic field information.

2. The MRI device according to claim 1, wherein the magnetic field sensors of the vector field camera comprise at least one magnetometer measuring optically detected magnetic resonance spectra and/or at least one Hall effect sensor configured for three-dimensional sensing.

3. The MRI device according to claim 1, wherein at least one electronic component of the vector field camera and/or the controller is positioned, at least partly, at least a predetermined distance away from the imaging region and/or outside a bore of the MRI device and/or a shielded room of the MRI device.

4. The MRI device according to claim 1, wherein the vector field camera is configured assuming that a sign of a projection of a magnetic field vector onto a nominal direction of the main magnetic field does not change in the imaging region, regarding the magnetic field, and the controller is configured to determine the magnetic field information based on the assumption.

5. The MRI device according to claim 1, wherein the controller is configured to control the vector field camera to periodically acquire sensor data to determine dynamic magnetic field information.

6. The MRI device according to claim 1, wherein:
   the controller is configured, for determining the magnetic field information, to fit the parameters of a magnetic field model to the sensor data at all measurement positions, and
   the magnetic field model comprises a series decomposition of the vector-valued magnetic field regarding vector-valued basis functions.

7. The MRI device according to claim 6, wherein:
   a number of magnetic field sensors is at least equal to a number of basic functions used in series decomposition;
   the controller is configured to use vector spherical harmonics as basis functions; and/or
   the series decomposition comprises at least terms of up to second order or up to third order.

8. The MRI device according to claim 7, wherein the series decomposition comprises at least terms of up to the third order.

9. The MRI device according to claim 1, wherein the controller is configured to detect, as at least one deviation, an inhomogeneity of the magnetic field, wherein at least one shimming device is controlled to at least partly compensate the inhomogeneity.

10. The MRI device according to claim 1, wherein, to determine a vector gradient impulse response function, the controller is configured to, for at least one gradient axis:
control the gradient coil arrangement to apply a predefined gradient pulse for the imaging region,
simultaneously output the predefined gradient pulse,
control the vector field camera to determine dynamic sensor data at the measurement positions, and
determine the vector gradient impulse response function from dynamic magnetic field information determined from the dynamic sensor data.

11. The MRI device according to claim 1, wherein the radio frequency arrangement comprises at least one local coil having a housing, wherein the magnetic field sensors are attached to and/or integrated into the housing.

12. The MRI device according to claim 11, wherein the at least one local coil includes a head coil and/or an extremity coil.

13. The MRI device according to claim 1, wherein the controller is configured to implement a correction measure in response to the magnetic field information indicating a deviation of the magnetic field from a reference field in the imaging region fulfilling a correction criterion.

14. A magnetic resonance imaging (MRI) device, comprising:
a main field unit configured to establish a main magnetic field in an imaging region;
a gradient coil assembly configured to generate a gradient field in the imaging region;
a radio frequency (RF) arrangement configured to send excitation signals to and receive magnetic resonance signals from the imaging region;
a field camera configured to determine magnetic field information in the imaging region, the field camera including multiple magnetic field sensors arranged at predefined measurement positions enclosing the imaging region, the field camera being a vector field camera configured to acquire vector-valued sensor data describing the magnetic field at each of the measurement positions three-dimensionally; and
a controller configured to:
receive sensor data for each of the predefined measurement positions,
calculate the magnetic field information for the imaging region based on the sensor data to determine the magnetic field information to three-dimensionally describe the magnetic field in the imaging region,
for determining the magnetic field information, fit the parameters of a magnetic field model to the sensor data at all measurement positions, the magnetic field model including a series decomposition of the vector-valued magnetic field regarding vector-valued basis functions, and
implement at least one calibration measure and/or correction measure based on the magnetic field information.

15. The MRI device according to claim 14, wherein the vector field camera comprises:
for magnetometers measuring optically detected magnetic resonance spectra, optical signal lines for each magnetic field sensor; and/or
for the magnetic field sensors, a power transmission device configured to work at a frequency of at least 1 GHz and/or not being a harmonic of the Larmor frequency of the magnetic resonance imaging device and/or using dielectric waveguides as power transmission lines.

* * * * *